US012599397B2

(12) United States Patent
Al-Jadda et al.

(10) Patent No.: US 12,599,397 B2
(45) Date of Patent: Apr. 14, 2026

(54) THROMBUS REMOVAL SYSTEMS AND ASSOCIATED METHODS

(71) Applicant: Shifamed Holdings, LLC, Campbell, CA (US)

(72) Inventors: Aadel Al-Jadda, San Carlos, CA (US); Tom Saul, Portland, OR (US); Kevin Muller, San Carlos, CA (US); Amr Salahieh, Saratoga, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 155 days.

(21) Appl. No.: 18/562,038

(22) PCT Filed: May 19, 2022

(86) PCT No.: PCT/US2022/030039
§ 371 (c)(1),
(2) Date: Nov. 17, 2023

(87) PCT Pub. No.: WO2022/240671
PCT Pub. Date: Nov. 24, 2022

(65) Prior Publication Data
US 2024/0238002 A1 Jul. 18, 2024

Related U.S. Application Data

(60) Provisional application No. 63/190,784, filed on May 19, 2021.

(51) Int. Cl.
*A61B 17/3203* (2006.01)
*A61B 17/00* (2006.01)
*A61B 17/22* (2006.01)

(52) U.S. Cl.
CPC .. *A61B 17/32037* (2013.01); *A61B 17/00234* (2013.01); *A61B 17/22* (2013.01);
(Continued)

(58) Field of Classification Search
CPC .............. A61B 17/00234; A61B 17/22; A61B 17/32037; A61B 17/221; A61B 17/3207;
(Continued)

(56) References Cited

U.S. PATENT DOCUMENTS

| | | | |
|---|---|---|---|
| 4,006,745 A | 2/1977 | Sorenson et al. | |
| 5,114,581 A | 5/1992 | Goldsmith et al. | |

(Continued)

FOREIGN PATENT DOCUMENTS

| | | |
|---|---|---|
| CN | 102727643 A | 10/2012 |
| CN | 105559854 A | 5/2016 |

(Continued)

OTHER PUBLICATIONS

Saul; U.S. Appl. No. 18/867,656 entitled "Thrombus removal systems and associated methods," filed Nov. 20, 2024.
(Continued)

*Primary Examiner* — Jocelin C Tanner
(74) *Attorney, Agent, or Firm* — Shay Glenn LLP

(57) ABSTRACT

The present technology relates to systems and methods for removing a thrombus from a blood vessel of a patient. In some embodiments, the present technology is directed to systems including an elongated catheter having a distal portion configured to be positioned within the blood vessel of the patient, a proximal portion configured to be external to the patient, and a lumen extending therebetween. The system can also include a fluid delivery mechanism coupled with a fluid lumen and configured to apply fluid to at least partially fragment the thrombus, and an aspiration mechanism fluidly coupled to an aspiration lumen and configured to aspirate the fragmented thrombus.

18 Claims, 7 Drawing Sheets

(52) U.S. Cl.
CPC .............. *A61B 2017/00238* (2013.01); *A61B 2017/00292* (2013.01); *A61B 2017/22079* (2013.01); *A61B 2217/005* (2013.01); *A61B 2217/007* (2013.01)

(58) Field of Classification Search
CPC ........... A61B 2017/00238; A61B 2017/00292; A61B 2017/22079; A61B 2017/2212; A61B 2017/2215; A61B 2017/2217; A61B 2017/22084; A61B 2017/22081; A61B 2017/22082; A61B 2017/320775; A61B 2217/005; A61B 2217/007; A61M 1/85; A61M 1/87; A61M 3/0283; A61M 2206/10
USPC .................................................. 606/159, 128
See application file for complete search history.

(56) References Cited

U.S. PATENT DOCUMENTS

| | | | |
|---|---|---|---|
| 5,135,482 | A | 8/1992 | Neracher |
| 5,651,776 | A | 7/1997 | Appling et al. |
| 5,662,671 | A | 9/1997 | Barbut et al. |
| 5,788,647 | A | 8/1998 | Eggers |
| 5,795,322 | A | 8/1998 | Boudewijn et al. |
| 5,993,469 | A | 11/1999 | McKenzie et al. |
| 6,004,339 | A | 12/1999 | Wijay |
| 6,053,870 | A | 4/2000 | Fulton, III |
| 6,059,825 | A | 5/2000 | Hobbs et al. |
| 6,074,374 | A | 6/2000 | Fulton |
| 6,086,534 | A | 7/2000 | Kesten |
| 6,283,950 | B1 | 9/2001 | Appling |
| 6,287,333 | B1 | 9/2001 | Appling et al. |
| 6,306,163 | B1 | 10/2001 | Fitz |
| 6,315,762 | B1 | 11/2001 | Recinella et al. |
| 6,524,300 | B2 | 2/2003 | Meglin |
| RE38,074 | E | 4/2003 | Recinella et al. |
| 6,582,447 | B1 | 6/2003 | Patel et al. |
| 6,733,489 | B2 | 5/2004 | Nutting et al. |
| 6,827,701 | B2 | 12/2004 | MacMahon et al. |
| 6,875,193 | B1 | 4/2005 | Bonnette et al. |
| 6,881,218 | B2 | 4/2005 | Beyer et al. |
| 6,942,635 | B2 | 9/2005 | Rosenblatt et al. |
| 6,966,886 | B2 | 11/2005 | Appling |
| 7,033,347 | B2 | 4/2006 | Appling |
| 7,131,981 | B2 | 11/2006 | Appling et al. |
| 7,163,533 | B2 | 1/2007 | Hobbs et al. |
| 7,217,256 | B2 | 5/2007 | Di Palma |
| 7,220,269 | B1 | 5/2007 | Ansel et al. |
| 7,273,478 | B2 | 9/2007 | Appling et al. |
| 7,279,000 | B2 | 10/2007 | Cartier et al. |
| 7,344,533 | B2 | 3/2008 | Pearson et al. |
| 7,347,852 | B2 | 3/2008 | Hobbs et al. |
| 7,419,487 | B2 | 9/2008 | Johnson et al. |
| 7,422,586 | B2 | 9/2008 | Morris et al. |
| 7,455,675 | B2 | 11/2008 | Schur et al. |
| 7,458,967 | B2 | 12/2008 | Appling et al. |
| 7,483,457 | B2 | 1/2009 | Howe et al. |
| 7,544,202 | B2 | 6/2009 | Cartier et al. |
| D595,892 | S | 7/2009 | Smith et al. |
| 7,563,247 | B2 | 7/2009 | Maguire et al. |
| D603,044 | S | 10/2009 | Appling et al. |
| 7,618,411 | B2 | 11/2009 | Appling |
| 7,717,900 | B2 | 5/2010 | di Palma |
| 7,722,635 | B2 | 5/2010 | Beyer et al. |
| 7,740,616 | B2 | 6/2010 | Smith et al. |
| 7,765,010 | B2 | 7/2010 | Chornenky et al. |
| 7,766,961 | B2 | 8/2010 | Patel et al. |
| 7,771,401 | B2 | 8/2010 | Hekmat et al. |
| 7,780,628 | B1 | 8/2010 | Keren et al. |
| D626,231 | S | 10/2010 | Perchik |
| 7,826,904 | B2 | 11/2010 | Appling et al. |
| 7,833,215 | B2 | 11/2010 | Appling |
| RE42,016 | E | 12/2010 | Chornenky et al. |
| D630,321 | S | 1/2011 | Hamilton |
| D631,154 | S | 1/2011 | Hamilton |
| 7,914,503 | B2 | 3/2011 | Goodson et al. |
| RE42,277 | E | 4/2011 | Jaafar et al. |
| 7,938,824 | B2 | 5/2011 | Chornenky et al. |
| 7,942,873 | B2 | 5/2011 | Kwan et al. |
| 7,947,019 | B2 | 5/2011 | Perchik et al. |
| D640,788 | S | 6/2011 | Appling |
| 7,993,325 | B2 | 8/2011 | Elkins et al. |
| D644,735 | S | 9/2011 | Elbe et al. |
| RE42,835 | E | 10/2011 | Chornenky et al. |
| RE43,009 | E | 12/2011 | Chornenky et al. |
| D650,475 | S | 12/2011 | Smith et al. |
| 8,114,070 | B2 | 2/2012 | Rubinsky et al. |
| 8,231,603 | B2 | 7/2012 | Hobbs et al. |
| 8,241,343 | B2 | 8/2012 | Douglass et al. |
| 8,317,773 | B2 | 11/2012 | Appling et al. |
| 8,328,760 | B2 | 12/2012 | Lareau |
| 8,328,768 | B2 | 12/2012 | Quigley et al. |
| 8,337,451 | B2 | 12/2012 | Lareau et al. |
| 8,337,470 | B2 | 12/2012 | Prasad et al. |
| 8,366,687 | B2 | 2/2013 | Girard et al. |
| 8,372,064 | B2 | 2/2013 | Douglass et al. |
| 8,377,011 | B2 | 2/2013 | Weaver et al. |
| D677,798 | S | 3/2013 | Hart et al. |
| 8,425,455 | B2 | 4/2013 | Nentwick |
| 8,472,011 | B2 | 6/2013 | Cronin et al. |
| 8,475,488 | B2 | 7/2013 | Cartier et al. |
| 8,496,644 | B2 | 7/2013 | Graffam et al. |
| 8,506,512 | B2 | 8/2013 | Aklog et al. |
| 8,518,011 | B2 | 8/2013 | Goodson et al. |
| 8,535,306 | B2 | 9/2013 | Pearson et al. |
| 8,574,204 | B2 | 11/2013 | Bourne et al. |
| 8,585,678 | B2 | 11/2013 | Elkins et al. |
| 8,585,950 | B2 | 11/2013 | Appling et al. |
| 8,586,897 | B2 | 11/2013 | Cronin |
| 8,603,070 | B1 | 12/2013 | Lareau et al. |
| 8,607,428 | B2 | 12/2013 | Nentwick et al. |
| 8,613,717 | B2 | 12/2013 | Aklog et al. |
| 8,632,534 | B2 | 1/2014 | Pearson et al. |
| 8,663,116 | B2 | 3/2014 | Hamilton |
| 8,679,074 | B2 | 3/2014 | Daly et al. |
| 8,734,374 | B2 | 5/2014 | Aklog et al. |
| 8,734,439 | B2 | 5/2014 | Gough et al. |
| 8,753,292 | B2 | 6/2014 | Ingold et al. |
| 8,753,335 | B2 | 6/2014 | Moshe et al. |
| 8,784,402 | B1 | 7/2014 | Lareau et al. |
| 8,858,497 | B2 | 10/2014 | Di Palma et al. |
| 8,864,754 | B2 | 10/2014 | Appling et al. |
| 8,903,488 | B2 | 12/2014 | Callas et al. |
| 8,926,573 | B2 | 1/2015 | Smith et al. |
| 8,956,383 | B2 | 2/2015 | Aklog et al. |
| 8,992,513 | B2 | 3/2015 | Delaney |
| 9,033,914 | B2 | 5/2015 | Haarala et al. |
| 9,050,435 | B2 | 6/2015 | Lareau et al. |
| 9,055,964 | B2 | 6/2015 | Cartier et al. |
| 9,078,665 | B2 | 7/2015 | Moss et al. |
| 9,084,619 | B2 | 7/2015 | Cronin et al. |
| D736,916 | S | 8/2015 | Appling et al. |
| 9,149,607 | B2 | 10/2015 | Scheibe et al. |
| 9,161,811 | B2 | 10/2015 | Cronin |
| 9,173,704 | B2 | 11/2015 | Hobbs et al. |
| 9,186,491 | B2 | 11/2015 | Casiello et al. |
| D744,639 | S | 12/2015 | Aklog et al. |
| 9,205,242 | B2 | 12/2015 | Nardone et al. |
| 9,206,283 | B1 | 12/2015 | Santerre et al. |
| D748,774 | S | 2/2016 | Caron |
| 9,254,173 | B2 | 2/2016 | Cronin et al. |
| 9,339,328 | B2 | 5/2016 | Ortiz et al. |
| 9,351,861 | B2 | 5/2016 | Sherburne |
| 9,358,378 | B2 | 6/2016 | Hanson et al. |
| 9,402,938 | B2 | 8/2016 | Aklog et al. |
| 9,408,620 | B2 | 8/2016 | Rosenbluth et al. |
| 9,414,881 | B2 | 8/2016 | Callas et al. |
| 9,440,046 | B2 | 9/2016 | Hobbs et al. |
| 9,440,047 | B1 | 9/2016 | Elberse et al. |
| 9,445,746 | B1 | 9/2016 | Elberse et al. |
| 9,447,892 | B2 | 9/2016 | Lareau et al. |
| 9,480,497 | B2 | 11/2016 | Ingold et al. |

(56) References Cited

U.S. PATENT DOCUMENTS

| | | |
|---|---|---|
| 9,675,406 B2 | 6/2017 | Moss et al. |
| 9,681,909 B2 | 6/2017 | Bhargav et al. |
| 9,700,332 B2 | 7/2017 | Marchand et al. |
| 9,700,368 B2 | 7/2017 | Callas et al. |
| 9,707,339 B2 | 7/2017 | Chartrand et al. |
| 9,757,197 B2 | 9/2017 | Cronin et al. |
| 9,764,115 B2 | 9/2017 | Tegg |
| 9,788,896 B2 | 10/2017 | Cronin et al. |
| 9,789,229 B1 | 10/2017 | Lareau et al. |
| D802,409 S | 11/2017 | Caron |
| 9,820,761 B2 | 11/2017 | Garrison et al. |
| 9,867,908 B2 | 1/2018 | Lareau et al. |
| 9,888,956 B2 | 2/2018 | Model et al. |
| 9,895,189 B2 | 2/2018 | Pearson |
| 9,895,524 B2 | 2/2018 | Lareau |
| 9,907,613 B2 | 3/2018 | Cronin et al. |
| 9,933,079 B2 | 4/2018 | Weaver et al. |
| 9,999,493 B2 | 6/2018 | Nguyen et al. |
| 10,004,531 B2 | 6/2018 | Rosenbluth et al. |
| 10,010,666 B2 | 7/2018 | Rubinsky et al. |
| 10,039,900 B2 | 8/2018 | di Palma et al. |
| 10,045,790 B2 | 8/2018 | Cox et al. |
| 10,098,651 B2 | 10/2018 | Marchand et al. |
| 10,105,477 B2 | 10/2018 | Davey et al. |
| 10,159,830 B2 | 12/2018 | Miller |
| 10,166,321 B2 | 1/2019 | Casiello et al. |
| 10,188,831 B2 | 1/2019 | Elberse et al. |
| 10,238,406 B2 | 3/2019 | Cox et al. |
| D847,623 S | 5/2019 | Caron |
| 10,279,112 B2 | 5/2019 | Houde et al. |
| 10,349,960 B2 | 7/2019 | Quick |
| D860,941 S | 9/2019 | Wheeler |
| 10,429,517 B1 | 10/2019 | Isham et al. |
| 10,493,257 B2 | 12/2019 | Chartrand et al. |
| 10,500,329 B2 | 12/2019 | Weaver et al. |
| 10,517,617 B2 | 12/2019 | Aklog et al. |
| 10,517,633 B2 | 12/2019 | Nash et al. |
| D879,957 S | 3/2020 | Zabar et al. |
| 10,610,678 B2 | 4/2020 | Martin |
| 10,660,691 B2 | 5/2020 | McKernon et al. |
| 10,782,425 B2 | 9/2020 | Isham |
| 10,786,270 B2 | 9/2020 | Yang et al. |
| 10,806,896 B2 | 10/2020 | Davies et al. |
| 10,835,715 B2 | 11/2020 | Cruz et al. |
| D908,204 S | 1/2021 | Casiello et al. |
| 10,905,492 B2 | 2/2021 | Neal |
| 10,912,885 B2 | 2/2021 | Maguire et al. |
| D916,280 S | 4/2021 | Swift |
| D916,281 S | 4/2021 | Swift |
| 11,000,682 B2 | 5/2021 | Merritt et al. |
| 11,065,018 B2 | 7/2021 | Busk et al. |
| 11,154,314 B2 | 10/2021 | Quick |
| 11,241,564 B2 | 2/2022 | Casiello et al. |
| 11,259,824 B2 | 3/2022 | Brady et al. |
| 11,433,218 B2 | 9/2022 | Quick et al. |
| 11,497,889 B2 | 11/2022 | Mixter et al. |
| D972,720 S | 12/2022 | Cote et al. |
| D972,723 S | 12/2022 | Swift et al. |
| 11,559,382 B2 | 1/2023 | Merritt et al. |
| 11,607,150 B2 | 3/2023 | Schweikert et al. |
| 11,648,020 B2 | 5/2023 | Cote et al. |
| 11,730,924 B2 | 8/2023 | Saadat et al. |
| 11,832,837 B2 | 12/2023 | Hauser |
| 11,864,779 B2 | 1/2024 | Dinh |
| 11,890,046 B2 | 2/2024 | Neal et al. |
| 11,950,835 B2 | 4/2024 | O'Brien et al. |
| 11,954,887 B2 | 4/2024 | Blau |
| 11,957,405 B2 | 4/2024 | Pearson |
| 11,986,196 B2 | 5/2024 | Wallace et al. |
| 11,986,382 B2 | 5/2024 | Merritt et al. |
| 11,992,643 B2 | 5/2024 | Lee et al. |
| 11,998,223 B2 | 6/2024 | Brady et al. |
| 12,002,065 B2 | 6/2024 | Look et al. |
| 12,004,731 B2 | 6/2024 | Duffy et al. |
| 12,011,186 B2 | 6/2024 | Stefanov |
| 12,016,580 B2 | 6/2024 | Quick et al. |
| 12,023,057 B2 | 7/2024 | Hauser |
| 12,023,058 B2 | 7/2024 | Casey |
| 12,029,442 B2 | 7/2024 | O'Malley |
| 12,032,735 B2 | 7/2024 | Rubin et al. |
| 12,042,160 B2 | 7/2024 | Yang et al. |
| 12,048,446 B2 | 7/2024 | Dwivedi et al. |
| 12,053,685 B2 | 8/2024 | Lockhart et al. |
| 12,064,130 B2 | 8/2024 | O'Malley et al. |
| 12,076,037 B2 | 9/2024 | Brady et al. |
| 12,080,020 B2 | 9/2024 | Blau |
| 12,096,938 B2 | 9/2024 | Hettel et al. |
| 12,096,951 B2 | 9/2024 | Barry et al. |
| 12,097,345 B2 | 9/2024 | Schultz et al. |
| 12,133,657 B2 | 11/2024 | Vale et al. |
| 12,144,515 B2 | 11/2024 | Nagireiter et al. |
| 12,150,659 B2 | 11/2024 | Look et al. |
| 12,156,665 B2 | 12/2024 | Look et al. |
| 12,156,666 B2 | 12/2024 | Trosper et al. |
| 12,156,667 B2 | 12/2024 | Trosper et al. |
| 12,171,449 B2 | 12/2024 | Lee |
| 12,184,353 B2 | 12/2024 | Collins |
| 12,186,064 B2 | 1/2025 | Strasser et al. |
| 12,198,330 B2 | 1/2025 | Blau |
| 12,201,506 B2 | 1/2025 | Buck et al. |
| 12,213,691 B2 | 2/2025 | Whelan |
| 12,214,189 B2 | 2/2025 | Lorenzo et al. |
| 12,220,138 B2 | 2/2025 | Whelan |
| 12,246,141 B2 | 3/2025 | Saadat et al. |
| 12,251,119 B2 | 3/2025 | Naglreiter et al. |
| 12,274,834 B2 | 4/2025 | Saadat et al. |
| 12,305,990 B2 | 5/2025 | Collins |
| D1,077,996 S | 6/2025 | Yang et al. |
| 12,462,425 B2 | 11/2025 | Blau |
| 2002/0058904 A1 | 5/2002 | Boock et al. |
| 2002/0111579 A1 | 8/2002 | Moutafis et al. |
| 2002/0123761 A1 | 9/2002 | Barbut et al. |
| 2002/0132076 A1 | 9/2002 | Stevens |
| 2003/0236517 A1 | 12/2003 | Appling |
| 2004/0097880 A1 | 5/2004 | Schur |
| 2005/0027262 A1 | 2/2005 | Appling et al. |
| 2005/0131343 A1 | 6/2005 | Abrams et al. |
| 2005/0143687 A1 | 6/2005 | Rosenblatt et al. |
| 2005/0165364 A1 | 7/2005 | DiMatteo et al. |
| 2005/0171510 A1 | 8/2005 | DiCarlo et al. |
| 2006/0184141 A1 | 8/2006 | Smith et al. |
| 2006/0270974 A1 | 11/2006 | Goff et al. |
| 2006/0282119 A1 | 12/2006 | Perchik |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2007/0021685 A1 | 1/2007 | Oepen et al. |
| 2007/0078391 A1 | 4/2007 | Wortley et al. |
| 2007/0106162 A1 | 5/2007 | Illyes et al. |
| 2007/0156135 A1 | 7/2007 | Rubinsky et al. |
| 2007/0173786 A1 | 7/2007 | Recinella et al. |
| 2007/0191825 A1 | 8/2007 | Cronin et al. |
| 2007/0198035 A1 | 8/2007 | Threlkeld |
| 2008/0114308 A1 | 5/2008 | di Palma et al. |
| 2008/0132884 A1 | 6/2008 | Rubinsky et al. |
| 2008/0132885 A1 | 6/2008 | Rubinsky et al. |
| 2008/0154186 A1 | 6/2008 | Appling et al. |
| 2008/0167649 A1 | 7/2008 | Edwards et al. |
| 2008/0167678 A1 | 7/2008 | Morsi |
| 2008/0172080 A1 | 7/2008 | Isham |
| 2008/0183202 A1 | 7/2008 | Isham |
| 2008/0208180 A1 | 8/2008 | Cartier et al. |
| 2008/0208236 A1 | 8/2008 | Hobbs et al. |
| 2008/0269774 A1 | 10/2008 | Garcia et al. |
| 2008/0287939 A1 | 11/2008 | Appling et al. |
| 2008/0294188 A1 | 11/2008 | Appling et al. |
| 2008/0300619 A1 | 12/2008 | Isham |
| 2009/0024190 A1 | 1/2009 | Irvine |
| 2009/0038752 A1 | 2/2009 | Weng et al. |
| 2009/0048577 A1 | 2/2009 | Gillies et al. |
| 2009/0076585 A1 | 3/2009 | Hendriksen et al. |
| 2009/0118683 A1 | 5/2009 | Hanson et al. |
| 2009/0131924 A1 | 5/2009 | Meyer et al. |
| 2009/0163926 A1 | 6/2009 | Sos |

(56) References Cited

U.S. PATENT DOCUMENTS

| | | |
|---|---|---|
| 2009/0171267 A1 | 7/2009 | Bonnette et al. |
| 2009/0221899 A1 | 9/2009 | Isham |
| 2009/0259220 A1 | 10/2009 | Appling et al. |
| 2009/0281477 A1 | 11/2009 | Mikus et al. |
| 2009/0306606 A1 | 12/2009 | Lancette et al. |
| 2009/0306625 A1 | 12/2009 | Pereira-Kamath et al. |
| 2009/0314724 A1 | 12/2009 | Nierich |
| 2010/0004623 A1 | 1/2010 | Hamilton et al. |
| 2010/0022947 A1 | 1/2010 | Hassidov et al. |
| 2010/0076302 A1 | 3/2010 | Gray et al. |
| 2010/0094201 A1 | 4/2010 | Mallaby |
| 2010/0114063 A1 | 5/2010 | Recinella et al. |
| 2010/0152725 A1 | 6/2010 | Pearson et al. |
| 2010/0168642 A1 | 7/2010 | Appling et al. |
| 2010/0204712 A1 | 8/2010 | Mallaby |
| 2010/0249771 A1 | 9/2010 | Pearson et al. |
| 2010/0249815 A1 | 9/2010 | Jantzen et al. |
| 2010/0250209 A1 | 9/2010 | Pearson et al. |
| 2010/0256487 A1 | 10/2010 | Hawkins et al. |
| 2010/0256546 A1 | 10/2010 | Davis et al. |
| 2010/0256630 A1 | 10/2010 | Hamilton et al. |
| 2011/0004295 A1 | 1/2011 | Wittens |
| 2011/0034886 A1 | 2/2011 | Elbe et al. |
| 2011/0040321 A1 | 2/2011 | Cartier |
| 2011/0060316 A1 | 3/2011 | DiCarlo |
| 2011/0105823 A1 | 5/2011 | Single et al. |
| 2011/0112527 A1 | 5/2011 | Hamilton et al. |
| 2011/0172644 A1 | 7/2011 | Zanoni et al. |
| 2011/0190734 A1 | 8/2011 | Graffam et al. |
| 2011/0190806 A1 | 8/2011 | Wittens |
| 2011/0213392 A1 | 9/2011 | Aklog et al. |
| 2011/0238057 A1 | 9/2011 | Moss et al. |
| 2011/0288529 A1 | 11/2011 | Fulton |
| 2012/0059210 A1 | 3/2012 | Frassica |
| 2012/0078232 A1 | 3/2012 | Schulting |
| 2012/0101471 A1 | 4/2012 | di Palma et al. |
| 2012/0184942 A1 | 7/2012 | Lareau |
| 2012/0193255 A1 | 8/2012 | Lareau et al. |
| 2012/0226271 A1 | 9/2012 | Callas et al. |
| 2012/0310230 A1 | 12/2012 | Willis |
| 2013/0131691 A1 | 5/2013 | Kozak et al. |
| 2013/0150811 A1 | 6/2013 | Horgan |
| 2013/0304082 A1 | 11/2013 | Aklog et al. |
| 2013/0310845 A1 | 11/2013 | Thor et al. |
| 2013/0324943 A1 | 12/2013 | Weaver et al. |
| 2013/0338608 A1 | 12/2013 | Moorehead et al. |
| 2014/0005699 A1 | 1/2014 | Bonnette et al. |
| 2014/0042154 A1 | 2/2014 | Cronin |
| 2014/0074049 A1 | 3/2014 | Veldhuijzen et al. |
| 2014/0228869 A1 | 8/2014 | Bonnette et al. |
| 2014/0303658 A1 | 10/2014 | Bonnette et al. |
| 2014/0364896 A1 | 12/2014 | Consigny |
| 2015/0057648 A1 | 2/2015 | Swift et al. |
| 2015/0068941 A1 | 3/2015 | Caron |
| 2015/0190615 A1 | 7/2015 | Shaltis |
| 2015/0230810 A1 | 8/2015 | Creighton et al. |
| 2015/0272622 A1 | 10/2015 | Carson et al. |
| 2015/0305810 A1 | 10/2015 | McElwee et al. |
| 2015/0320488 A1 | 11/2015 | Moshe et al. |
| 2015/0359547 A1 | 12/2015 | Vale et al. |
| 2016/0022371 A1 | 1/2016 | Sauer et al. |
| 2016/0030708 A1 | 2/2016 | Casiello et al. |
| 2016/0058493 A1 | 3/2016 | Neal et al. |
| 2016/0106501 A1 | 4/2016 | Appling |
| 2016/0114128 A1 | 4/2016 | Lancette |
| 2016/0114129 A1 | 4/2016 | Lancette |
| 2016/0135712 A1 | 5/2016 | Holochwost et al. |
| 2016/0135829 A1 | 5/2016 | Holochwost et al. |
| 2016/0235974 A1 | 8/2016 | Holochwost et al. |
| 2016/0271321 A1 | 9/2016 | Chambers et al. |
| 2016/0317797 A1 | 11/2016 | Smith et al. |
| 2016/0346472 A1 | 12/2016 | Mitchell et al. |
| 2017/0136158 A1 | 5/2017 | Culhane et al. |
| 2017/0172603 A1 | 6/2017 | Bonnette et al. |
| 2017/0231655 A1 | 8/2017 | Aljuri et al. |
| 2017/0303949 A1 | 10/2017 | Ribo Jacobi et al. |
| 2017/0333060 A1 | 11/2017 | Panian |
| 2017/0333076 A1 | 11/2017 | Bruzzi et al. |
| 2018/0064526 A1 | 3/2018 | Walzman |
| 2018/0071014 A1 | 3/2018 | Neal et al. |
| 2018/0071492 A1 | 3/2018 | Laby et al. |
| 2018/0098782 A1 | 4/2018 | Farago |
| 2018/0103974 A1 | 4/2018 | Osborne et al. |
| 2018/0116710 A1 | 5/2018 | Pearson |
| 2018/0207397 A1 | 7/2018 | Look et al. |
| 2018/0272050 A1 | 9/2018 | Laureau et al. |
| 2018/0291882 A1 | 10/2018 | Algawi et al. |
| 2018/0317899 A1 | 11/2018 | Zada |
| 2018/0344987 A1 | 12/2018 | Lancette et al. |
| 2019/0008550 A1 | 1/2019 | Yamanouchi |
| 2019/0021856 A1 | 1/2019 | High |
| 2019/0029791 A1 | 1/2019 | Walzman |
| 2019/0030319 A1 | 1/2019 | Raines |
| 2019/0038300 A1 | 2/2019 | Savastano et al. |
| 2019/0054284 A1 | 2/2019 | Smith et al. |
| 2019/0076623 A1 | 3/2019 | Mackay et al. |
| 2019/0083169 A1 | 3/2019 | Single et al. |
| 2019/0143085 A1 | 5/2019 | Isham |
| 2019/0167287 A1 | 6/2019 | Vale et al. |
| 2019/0175939 A1 | 6/2019 | Isham et al. |
| 2019/0217058 A1 | 7/2019 | Swift |
| 2019/0262031 A1 | 8/2019 | Efremkin |
| 2019/0290323 A1 | 9/2019 | Chun et al. |
| 2019/0321656 A1 | 10/2019 | Isham et al. |
| 2019/0365248 A1 | 12/2019 | Mueller et al. |
| 2019/0365464 A1 | 12/2019 | Govari et al. |
| 2020/0022712 A1 | 1/2020 | Deville et al. |
| 2020/0030501 A1 | 1/2020 | Minskoff |
| 2020/0038057 A1 | 2/2020 | Rai et al. |
| 2020/0054864 A1 | 2/2020 | Vrancken Peeters et al. |
| 2020/0085453 A1 | 3/2020 | Porter et al. |
| 2020/0101326 A1 | 4/2020 | Zeringue |
| 2020/0107843 A1 | 4/2020 | Goertz et al. |
| 2020/0164117 A1 | 5/2020 | Culhane et al. |
| 2020/0246014 A1 | 8/2020 | Walzman |
| 2020/0253670 A1 | 8/2020 | Doisneau et al. |
| 2020/0276415 A1 | 9/2020 | Tang et al. |
| 2020/0289722 A1 | 9/2020 | Culbert et al. |
| 2020/0352286 A1 | 11/2020 | Galindo et al. |
| 2020/0397959 A1 | 12/2020 | Douglas et al. |
| 2021/0001090 A1 | 1/2021 | Tran et al. |
| 2021/0008354 A1 | 1/2021 | Bhamanyar |
| 2021/0069468 A1 | 3/2021 | Keating et al. |
| 2021/0085931 A1 | 3/2021 | Green et al. |
| 2021/0121188 A1* | 4/2021 | Yurek ............ A61B 17/22 |
| 2021/0128182 A1 | 5/2021 | Teigen et al. |
| 2021/0128893 A1 | 5/2021 | Twomey et al. |
| 2021/0145445 A9 | 5/2021 | Goldsmith |
| 2021/0153884 A1 | 5/2021 | Casey et al. |
| 2021/0154433 A1 | 5/2021 | Casey et al. |
| 2021/0186541 A1 | 6/2021 | Thress |
| 2021/0186547 A1 | 6/2021 | Kassab et al. |
| 2021/0196292 A1* | 7/2021 | Vale ............ A61M 25/0045 |
| 2021/0220006 A1 | 7/2021 | Mitchell |
| 2021/0298773 A1 | 9/2021 | Echarri et al. |
| 2021/0315639 A1 | 10/2021 | Manucherhabadi et al. |
| 2021/0346040 A1 | 11/2021 | Panian |
| 2021/0361314 A1 | 11/2021 | Teigen et al. |
| 2021/0378694 A1 | 12/2021 | Thress et al. |
| 2021/0393277 A1 | 12/2021 | Vale et al. |
| 2022/0000500 A1 | 1/2022 | Arad Hadar et al. |
| 2022/0008022 A1 | 1/2022 | Raman et al. |
| 2022/0039815 A1 | 2/2022 | Thress et al. |
| 2022/0054151 A1 | 2/2022 | Shifflette |
| 2022/0061870 A1 | 3/2022 | Mintz |
| 2022/0105333 A1 | 4/2022 | Bourne et al. |
| 2022/0125450 A1 | 4/2022 | Sirhan et al. |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0168000 A1 | 6/2022 | Naglreiter et al. |
| 2022/0175404 A1 | 6/2022 | Mintz et al. |
| 2022/0193373 A1 | 6/2022 | Clark et al. |
| 2022/0202506 A1 | 6/2022 | Sganga et al. |

(56)  References Cited

U.S. PATENT DOCUMENTS

| | | | |
|---|---|---|---|
| 2022/0249151 A1 | 8/2022 | Forrest et al. |
| 2022/0257268 A1 | 8/2022 | Culbert et al. |
| 2022/0287729 A1 | 9/2022 | Phillips et al. |
| 2023/0030606 A1 | 2/2023 | Swift et al. |
| 2023/0088977 A1 | 3/2023 | Fischell et al. |
| 2023/0148876 A1 | 5/2023 | Robinson et al. |
| 2023/0149035 A1 | 5/2023 | Sirhan et al. |
| 2023/0149073 A1 | 5/2023 | Forrest et al. |
| 2023/0218310 A1 | 7/2023 | Scheinblum et al. |
| 2023/0241302 A1 | 8/2023 | Merritt et al. |
| 2023/0248380 A1 | 8/2023 | Long et al. |
| 2023/0285081 A1 | 9/2023 | Wagner et al. |
| 2023/0310751 A1 | 10/2023 | Merritt et al. |
| 2023/0329777 A1 | 10/2023 | Single et al. |
| 2023/0346416 A1 | 11/2023 | Berrada et al. |
| 2023/0355938 A1 | 11/2023 | Merritt et al. |
| 2024/0000469 A1 | 1/2024 | Teigen et al. |
| 2024/0074804 A1 | 3/2024 | Neal et al. |
| 2024/0138903 A1 | 5/2024 | Pearson |
| 2024/0156473 A1 | 5/2024 | Aklog et al. |
| 2024/0164804 A1 | 5/2024 | Jenson et al. |
| 2024/0164805 A1 | 5/2024 | Jenson et al. |
| 2024/0173042 A1 | 5/2024 | Yang et al. |
| 2024/0173063 A1 | 5/2024 | Neal, II et al. |
| 2024/0188972 A1 | 6/2024 | Vale et al. |
| 2024/0189544 A1 | 6/2024 | Casey et al. |
| 2024/0197347 A1 | 6/2024 | Saadat et al. |
| 2024/0197349 A1 | 6/2024 | Kelly et al. |
| 2024/0197416 A1 | 6/2024 | Gonzalez et al. |
| 2024/0197978 A1 | 6/2024 | Yee |
| 2024/0198060 A1 | 6/2024 | Casey et al. |
| 2024/0198072 A1 | 6/2024 | Merritt et al. |
| 2024/0216600 A1 | 7/2024 | Lenihan et al. |
| 2024/0245417 A1 | 7/2024 | Baron et al. |
| 2024/0245424 A1 | 7/2024 | Casey et al. |
| 2024/0261492 A1 | 8/2024 | Yang et al. |
| 2024/0268844 A1 | 8/2024 | Casey et al. |
| 2024/0285846 A1 | 8/2024 | Su et al. |
| 2024/0299707 A1 | 9/2024 | Humbert et al. |
| 2024/0307659 A1 | 9/2024 | Saadat et al. |
| 2024/0341785 A1 | 10/2024 | Trosper et al. |
| 2024/0341786 A1 | 10/2024 | Trosper et al. |
| 2024/0382223 A1 | 11/2024 | Gilvarry et al. |
| 2025/0064322 A1 | 2/2025 | Vale et al. |
| 2025/0152189 A1 | 5/2025 | Janardhan et al. |
| 2025/0160859 A1 | 5/2025 | Janardhan et al. |
| 2025/0169834 A1 | 5/2025 | Janardhan et al. |
| 2025/0177692 A1 | 6/2025 | Yee et al. |

FOREIGN PATENT DOCUMENTS

| | | | |
|---|---|---|---|
| CN | 211068270 U | 7/2020 |
| CN | 111481262 A | 8/2020 |
| CN | 111528983 A | 8/2020 |
| DE | 4018736 A1 | 1/1992 |
| JP | H0197951 A | 4/1989 |
| JP | 2007117384 A | 5/2007 |
| JP | 2010505542 A | 2/2010 |
| JP | 2013154171 A | 8/2013 |
| WO | WO89/05665 A2 | 6/1989 |
| WO | WO94/016706 A1 | 8/1994 |
| WO | WO2000/006224 A1 | 2/2000 |
| WO | WO02/26289 A1 | 4/2002 |
| WO | WO2003/084596 A1 | 10/2003 |
| WO | WO2003/092537 A2 | 11/2003 |
| WO | WO2004/000099 A2 | 12/2003 |
| WO | WO2004/004546 A2 | 1/2004 |
| WO | WO2004/043220 A2 | 5/2004 |
| WO | WO2004/050144 A2 | 6/2004 |
| WO | WO2004/093941 A2 | 11/2004 |
| WO | WO2006/012242 A2 | 2/2006 |
| WO | WO2006/012243 A2 | 2/2006 |
| WO | WO2006/012244 A2 | 2/2006 |
| WO | WO2006/086516 A2 | 8/2006 |
| WO | WO2007/017876 A2 | 2/2007 |
| WO | WO2007/041471 A2 | 4/2007 |
| WO | WO2007/085025 A2 | 7/2007 |
| WO | WO2008/124790 A2 | 10/2008 |
| WO | WO2008/147760 A1 | 12/2008 |
| WO | WO2009/035582 A1 | 3/2009 |
| WO | WO2009/046439 A2 | 4/2009 |
| WO | WO2009/062105 A2 | 5/2009 |
| WO | WO2009/114826 A2 | 9/2009 |
| WO | WO2009/131583 A1 | 10/2009 |
| WO | WO2009/137800 A2 | 11/2009 |
| WO | WO2009/155526 A2 | 12/2009 |
| WO | WO2010/008834 A2 | 1/2010 |
| WO | WO2010/085765 A2 | 7/2010 |
| WO | WO2010/093692 A2 | 8/2010 |
| WO | WO2010/117806 A1 | 10/2010 |
| WO | WO2010/138919 A2 | 12/2010 |
| WO | WO2011/022674 A2 | 2/2011 |
| WO | WO2011/103096 A2 | 8/2011 |
| WO | WO2011/103133 A2 | 8/2011 |
| WO | WO2012/051433 A2 | 4/2012 |
| WO | WO2013/119662 A1 | 8/2013 |
| WO | WO2014/047626 A2 | 3/2014 |
| WO | WO2015/196156 A1 | 12/2015 |
| WO | WO2016/164930 A1 | 10/2016 |
| WO | WO2017/070702 A1 | 4/2017 |
| WO | WO2017/106877 A1 | 6/2017 |
| WO | WO2018/033401 A1 | 2/2018 |
| WO | WO2018/080590 A1 | 5/2018 |
| WO | WO2018/094050 A2 | 5/2018 |
| WO | WO2019/050765 A1 | 3/2019 |
| WO | WO2020/036809 A1 | 2/2020 |
| WO | WO2020/206366 A1 | 10/2020 |
| WO | WO2021/076954 A1 | 4/2021 |
| WO | WO2021/127202 A1 | 6/2021 |
| WO | WO2021/178696 A1 | 9/2021 |
| WO | WO20212/48042 A1 | 12/2021 |
| WO | WO2022/032173 A1 | 2/2022 |
| WO | WO2022/103848 A1 | 5/2022 |
| WO | WO2022/109021 A1 | 5/2022 |
| WO | WO2022/109034 A1 | 5/2022 |
| WO | WO2022/120270 A1 | 6/2022 |
| WO | WO2022/251678 A1 | 12/2022 |
| WO | WO2022/261448 A1 | 12/2022 |
| WO | WO2022/261462 A1 | 12/2022 |
| WO | WO2023/288268 A1 | 1/2023 |
| WO | WO2023/035013 A1 | 3/2023 |
| WO | WO2023/049802 A1 | 3/2023 |
| WO | WO2023/137341 A1 | 7/2023 |
| WO | WO2023/147353 A1 | 8/2023 |
| WO | WO2023/150730 A2 | 8/2023 |
| WO | WO2023/154612 A2 | 8/2023 |
| WO | WO2023/168415 A1 | 9/2023 |
| WO | WO2023/178212 A2 | 9/2023 |
| WO | WO2023/192925 A2 | 10/2023 |
| WO | WO2023/215779 A2 | 11/2023 |
| WO | WO2023/220633 A2 | 11/2023 |

OTHER PUBLICATIONS

Dala et al.; U.S. Appl. No. 18/994,012 entitled "Thrombus removal systems and associated methods," filed Jan. 13, 2021.

Al-Jadda et al.; 19/106,171 entitled "Thrombus removal systems and associated methods," filed Feb. 24, 2025.

Al-Jadda et al.; U.S. Appl. No. 19/106,174 entitled "Contrast injection and visualization systems and methods for thrombus removal device," filed Feb. 24, 2025.

Gunning; U.S. Appl. No. 19/106,179 entitled "Thrombus removal systems and associated methods," filed Feb. 24, 2025.

Al-Jadda et al.; U.S. Appl. No. 18/568,656 entitled "Thrombus removal systems and associated meethods," filed Dec. 8, 2023.

Al-Jadda et al.; U.S. Appl. No. 18/568,681 entitled "Thrombus removal systems and associated methods," filed Dec. 8, 2023.

Salahieh et al.; U.S. Appl. No. 18/688,941 entitled "Thrombus removal systems and associated methods," filed Mar. 4, 2024.

Illindala.; U.S. Appl. No. 18/773,208 enttitled "Thrombus removal systems and associated methods," filed Jul. 15, 2024.

Gunning et al.; U.S. Appl. No. 18/835,686 entitled "Thrombus removal systems and associated methods," filed Aug. 2, 2024.

(56) References Cited

OTHER PUBLICATIONS

Tanyildizi et al.; In vitro testing of a funnel-shaped tip catheter model to decrease clot migration during mechanical thrombectomy; Scientific Reports; 10(1); 7 pages; Jan. 20, 2020.

Anenberg et al.; Optogenetic stimulation of GABA neurons can decrease local neuronal activity while increasing cortical blood flow; Journal of Cerebral Blood Flow & Metabolism; 35(10); pp. 1579-1586; Oct. 2015.

Eucker et al.; Phase plane analysis of left ventricular hemodynamics; Journal of Applied Physiology; 90(6); pp. 2238-2244; Jun. 1, 2001.

Kondo et al.; Pulmonary hypertension: diagnosis, management, and treatment; Nagoya journal of medical science; 81(1); pp. 19-30; Feb. 2019.

Gunning et al.; U.S. Appl. No. 18/847,594 entitled "Thrombus removal systems and associated methods," filed Sep. 16, 2024.

Al-Jadda et al.; U.S. Appl. No. 18/864,484 entitled "Thrombus removal systems and associated methods," filed Nov. 8, 2024.

Saul; U.S. Appl. No. 18/686,616 entitled "Thrombus removal systems and associated methods," filed Nov. 22, 2024.

Chen et al.; Formation of nanocrystalline AZ31B Mg alloys via cryogenic rotary swaging; Journal of Magnesium and Alloys; 11(5); pp. 1580-1591; May 1, 2023.

* cited by examiner

Section A-A

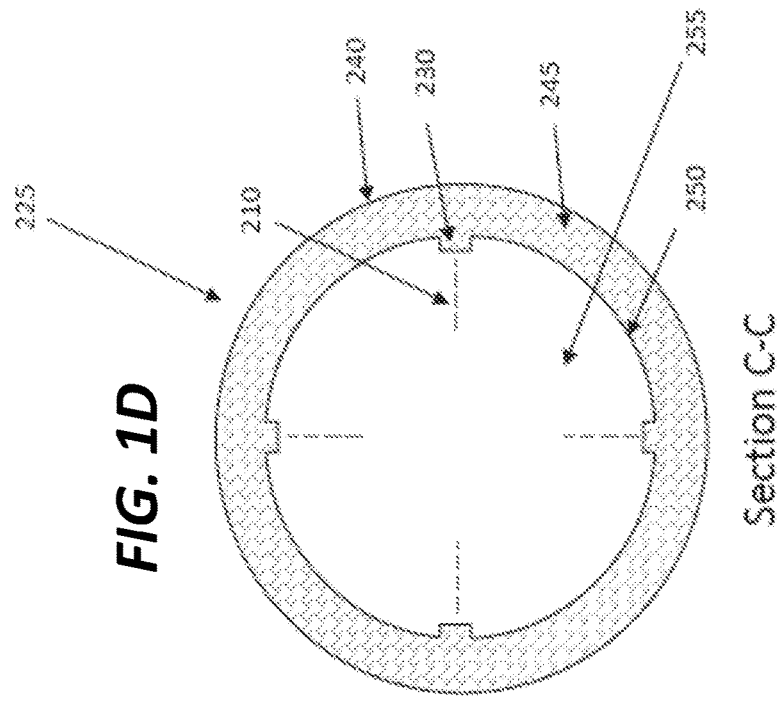
*FIG. 1D*
Section C-C
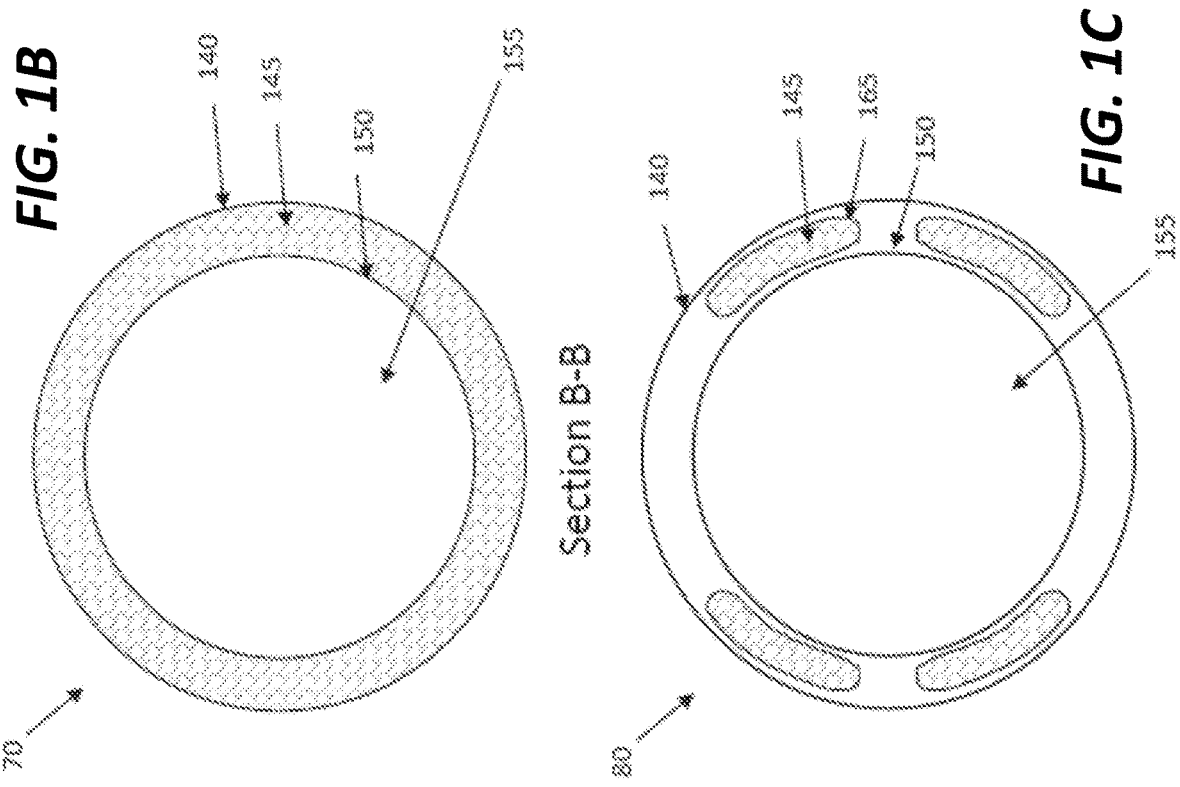
*FIG. 1B*
*FIG. 1C*
Section B-B

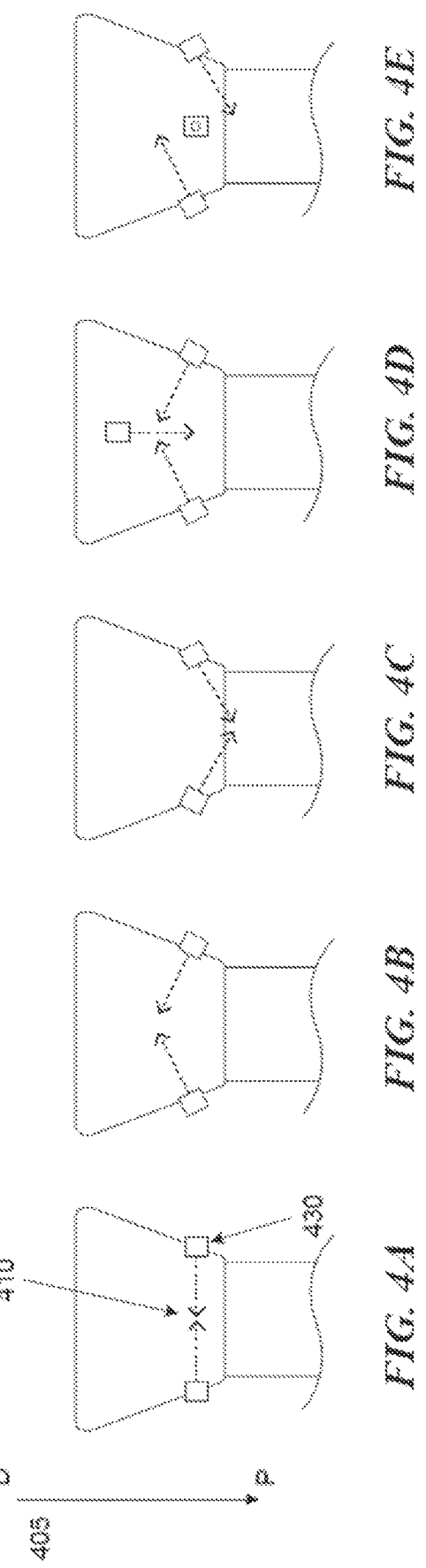
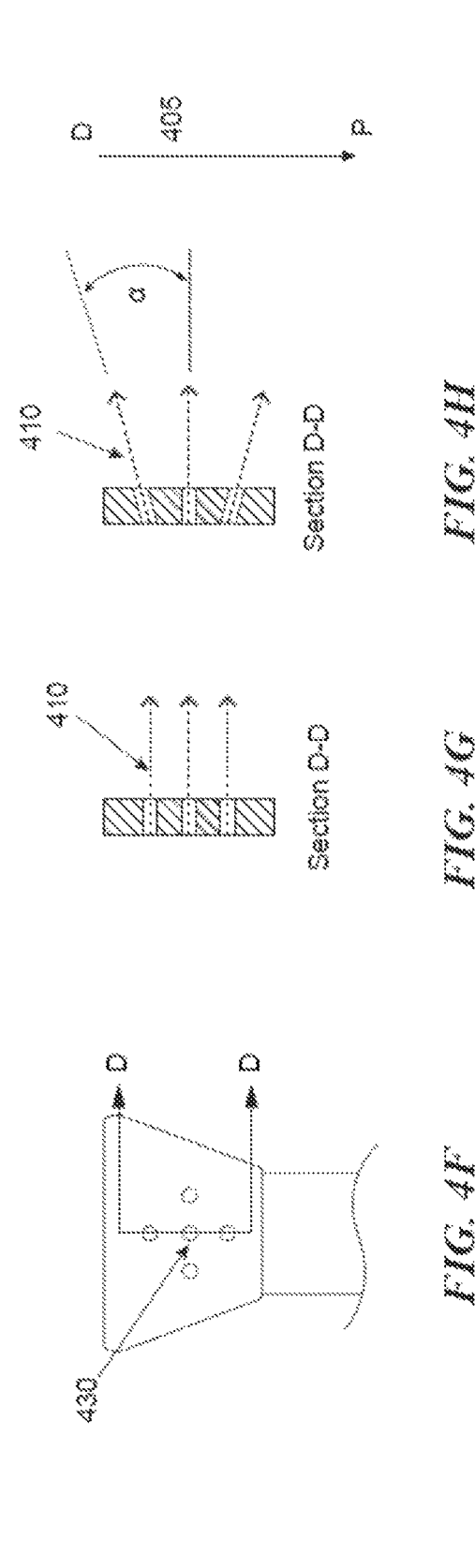
*FIG. 4E*
*FIG. 4D*
*FIG. 4C*
*FIG. 4B*
*FIG. 4A*
*FIG. 4H*
*FIG. 4G*
*FIG. 4F*

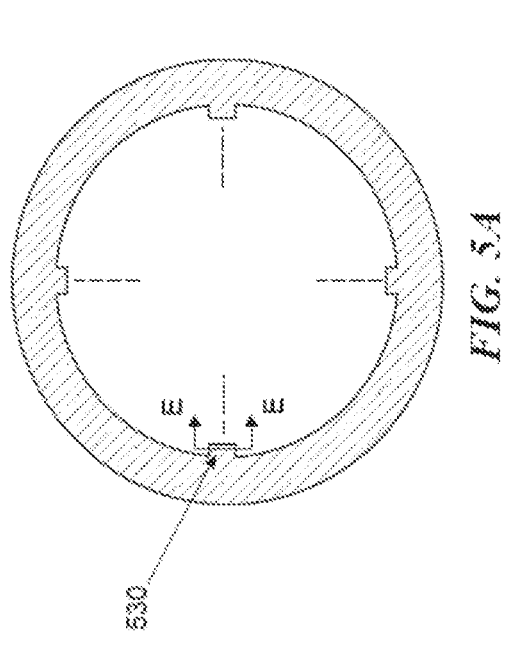
*FIG. 5A*
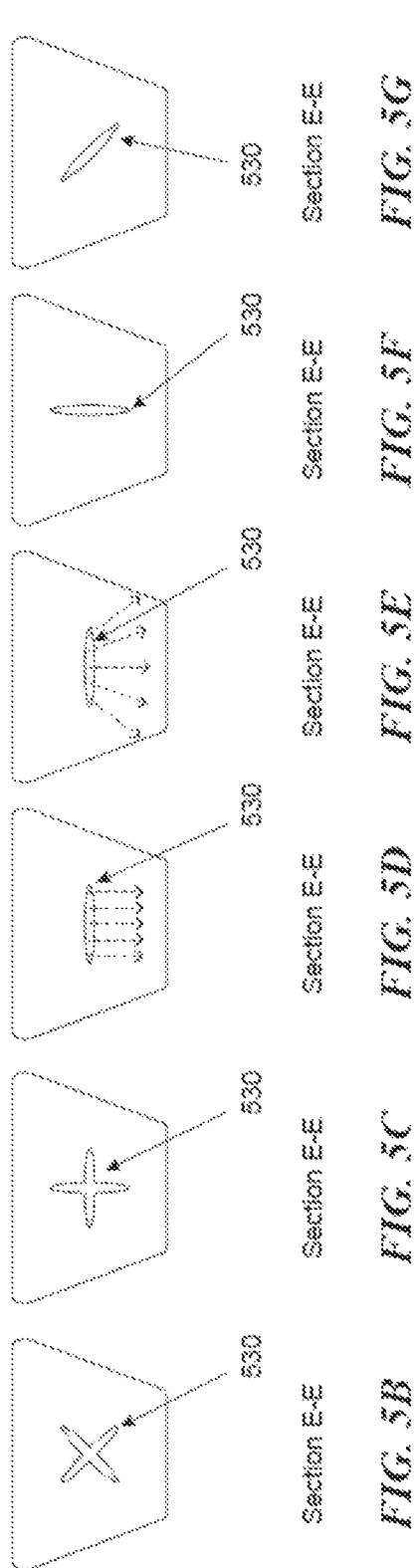
530          Section E-E          *FIG. 5B*
530          Section E-E          *FIG. 5C*
530          Section E-E          *FIG. 5D*
530          Section E-E          *FIG. 5E*
530          Section E-E          *FIG. 5F*
530          Section E-E          *FIG. 5G*

THROMBUS REMOVAL SYSTEMS AND ASSOCIATED METHODS

RELATED APPLICATIONS

This application is related to International Application No. PCT/US2021/020915, filed Mar. 4, 2021, and U.S. Application No. 63/190,784, filed May 19, 2021, the disclosures of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

The present technology generally relates to medical devices and, in particular, to systems including aspiration and fluid delivery mechanisms and associated methods for removing a thrombus from a mammalian blood vessel.

BACKGROUND

Thrombotic material may lead to a blockage in fluid flow within the vasculature of a mammal. Such blockages may occur in varied regions within the body, such as within the pulmonary system, peripheral vasculature, deep vasculature, or brain. Pulmonary embolisms typically arise when a thrombus originating from another part of the body (e.g., a vein in the pelvis or leg) becomes dislodged and travels to the lungs. Anticoagulation therapy is the current standard of care for treating pulmonary embolisms, but may not be effective in some patients. Additionally, conventional devices for removing thrombotic material may not be capable of navigating the vascular anatomy of the lungs, may not be effective in removing thrombotic material, and/or may lack the ability to provide sensor data or other feedback to the clinician during the thrombectomy procedure.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1-1E illustrate various views of a portion of a thrombus removal system including a distal portion of an elongated catheter configured in accordance with an embodiment of the present technology.

FIGS. 2A-2E illustrate plan views of various configurations of irrigation ports and fluid streams of a thrombus removal system according to embodiments of the present technology.

FIGS. 4A-4H illustrate an elevation view of various configurations of irrigation ports and fluid streams of a thrombus removal system according to embodiments of the present technology.

FIGS. 5A-5G illustrate various configurations of irrigation ports of a thrombus removal system according to embodiments of the present technology.

SUMMARY OF THE DISCLOSURE

Figures 1, 1A:
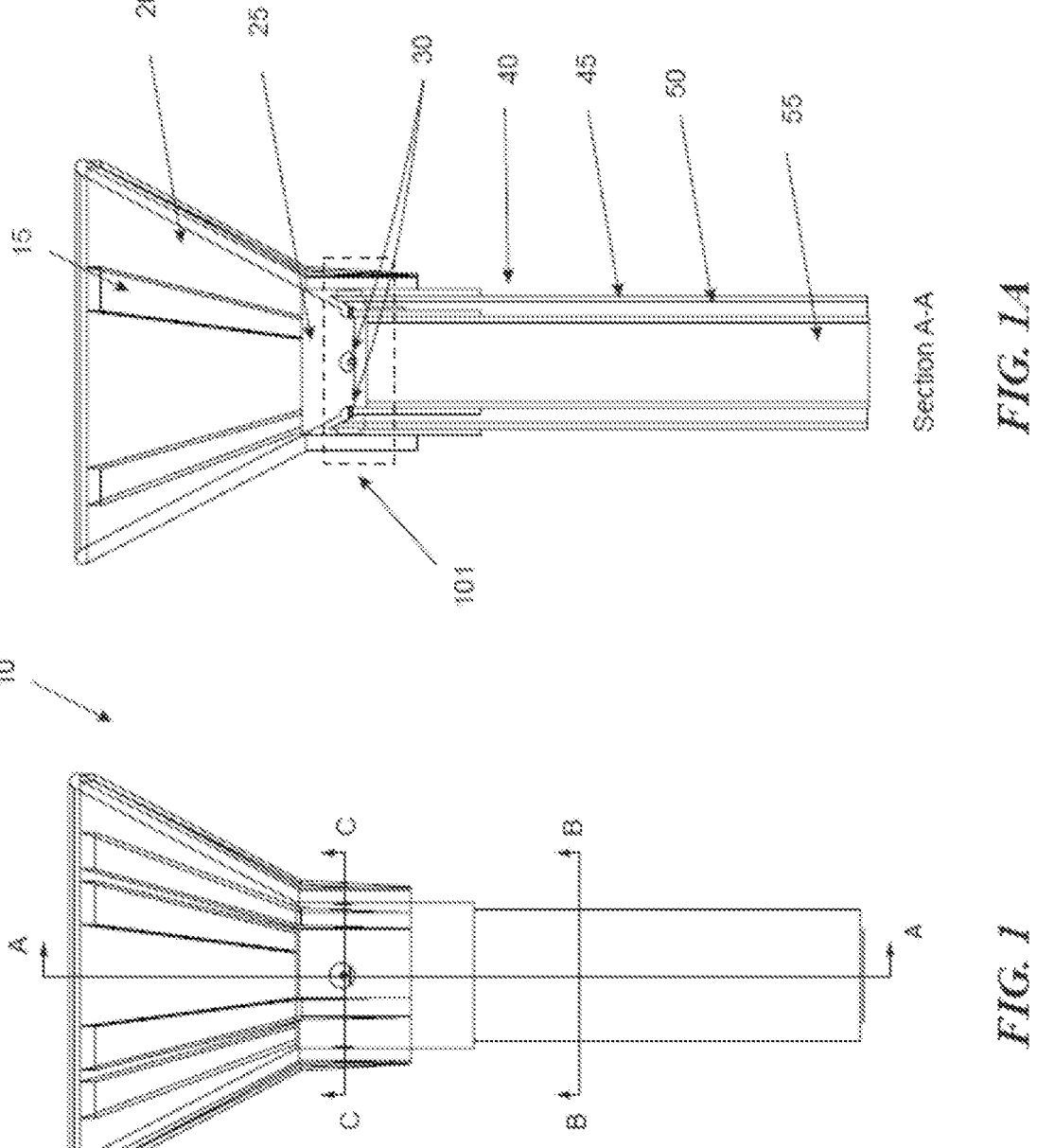

A thrombus removal system is provided, comprising an elongated catheter device including a distal portion configured to be positioned within a blood vessel of a patient, the distal portion comprising an inner wall forming an aspiration lumen, and an outer wall, a manifold formed near a distal end of the fluid lumen, the manifold including at least two fluid ports formed therein and adapted for fluid communication with the fluid lumen to direct respective fluid streams from the at least two fluid ports, a proximal portion configured to be positioned external to the patient, the aspiration lumen extending from the distal portion to the proximal portion, an aspiration mechanism positioned external to the patient and fluidly coupled with the aspiration lumen, the aspiration mechanism configured to reduce a pressure at the distal portion (a) to engage a thrombus therewith and/or (b) to draw the thrombus and/or thrombus fragments proximally, and a fluid delivery mechanism configured to supply fluid through the fluid lumen.

In some embodiments, the inner wall and the outer wall are concentrically arranged such that the fluid lumen is generally annular in cross-section.

In one example, the system further includes at least one fluid wall disposed in the space between the inner and outer walls, the at least one fluid wall forming the fluid lumen.

In some examples, the irrigation manifold is formed from the inner wall and the outer wall.

In one embodiment, the at least two fluid ports are formed within the inner wall of the manifold.

In some embodiments, the inner wall has a first thickness in a first region within the manifold, and a second thickness proximal to the first region. In other examples, the first thickness is greater than the second thickness. In one embodiment, the first thickness is about twice that of the second thickness. In some implementations, the first thickness ranges from 0.10 mm to 0.60 mm and the second thickness ranges from 0.20 mm to 0.70 mm. In some embodiments, the first thickness is selected to provide a generally laminar flow for the respective fluid streams.

In one example, a cross-sectional dimension of the two or more ports varies along its length.

In some implementations, the two or more ports are conical along their lengths.

In one embodiment, a smallest dimension of the two or more ports is positioned at a distal end of the two or more ports.

In some examples, the respective fluid streams are configured to intersect near at least one intersection region.

In one embodiment, at least one intersection region is located proximally with respect to at least one of the at least two fluid ports.

In other examples, at least one intersection region is located distally with respect to at least one of the at least two fluid ports.

In some embodiments, the irrigation manifold is configured to increase a flow rate of the fluid in the fluid lumen. In another embodiment, the irrigation manifold is configured to increase a pressure of the fluid in the fluid lumen.

In some embodiments, the system further includes a funnel positioned at a distal end of the distal portion, the funnel being configured to engage with the thrombus.

In one embodiment, the irrigation manifold is disposed proximally of the manifold. In other embodiments, the irrigation manifold is integrated into the funnel.

A method for removing a thrombus from a blood vessel of a patient is provided, the method comprising introducing a distal portion of an elongate catheter to a thrombus location in a blood vessel, drawing at least a section of the thrombus into the distal portion, and directing fluid toward the thrombus at between 10-15 m/s from at least two different points along respective fluid paths that intersect.

In some embodiments, the drawing is by suction applied via an aspiration lumen of the elongate catheter.

In another embodiment, directing fluid further comprises directing one of the respective fluid paths proximally. In some embodiments, directing fluid further comprises directing one of the respective fluid paths distally. In other embodiments, directing fluid further comprises directing a first fluid path proximally and a second fluid path distally. In another example, directing fluid further comprises directing a first fluid path proximally and a second fluid path orthogonally with respect to an aspiration flow axis.

A method for removing a thrombus from a blood vessel of a patient is also provided, the method comprising introducing a distal portion of an elongate catheter to a thrombus location in a blood vessel, drawing at least a section of the thrombus into the distal portion, delivering fluid from a fluid delivery mechanism into a fluid lumen of the elongate catheter, increasing a flow rate of the fluid with an irrigation manifold disposed at a distal end of the fluid lumen, and directing at least two fluid streams with ports disposed in the irrigation manifold.

In some embodiments, the drawing is by suction applied via an aspiration lumen of the elongate catheter.

In one embodiment, the at least two fluid streams are directed proximally with the ports. In other embodiments, the at least two fluid streams are directed distally with the ports. In some examples, the at least two fluid streams are directed orthogonally relative to a longitudinal axis of the elongate catheter with the ports. In another embodiment, the at least two fluid streams are directed towards an intersection region.

In some embodiments, the flow rate of the at least two fluid streams comprises 10-15 m/s. In another embodiment, the flow rate of the at least two fluid streams comprises 12-15 m/s.

DETAILED DESCRIPTION

The present technology is generally directed to thrombus removal systems and associated methods. A system configured in accordance with an embodiment of the present technology can include, for example, an elongated catheter having a distal portion configured to be positioned within a blood vessel of the patient, a proximal portion configured to be external to the patient, a fluid delivery mechanism configured to fragment the thrombus with pressurized fluid, an aspiration mechanism configured to aspirate the fragments of the thrombus, and one or more lumens extending at least partially from the proximal portion to the distal portion.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to the figures.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Although some embodiments herein are described in terms of thrombus removal, it will be appreciated that the present technology can be used and/or modified to remove other types of emboli that may occlude a blood vessel, such as fat, tissue, or a foreign substance. Additionally, although some embodiments herein are described in the context of thrombus removal from a pulmonary artery (e.g., pulmonary embolectomy), the technology may be applied to removal of thrombi and/or emboli from other portions of the vasculature (e.g., in neurovascular, coronary, or peripheral applications). Moreover, although some embodiments are discussed in terms of maceration of a thrombus with a fluid, the present technology can be adapted for use with other techniques for breaking up a thrombus into smaller fragments or particles (e.g., ultrasonic, mechanical, enzymatic, etc.).

The headings provided herein are for convenience only and do not interpret the scope or meaning of the claimed present technology.

Systems for Thrombus Removal

As provided above, the present technology is generally directed to thrombus removal systems. Such systems include an elongated catheter having a distal portion positionable within a blood vessel of the patient (e.g., an artery or vein), a proximal portion positionable outside the patient's body, a fluid delivery mechanism configured to fragment the thrombus with pressurized fluid, an aspiration mechanism configured to aspirate the fragments of the thrombus, and one or more lumens extending at least partially from the proximal portion to the distal portion. In some embodiments, the systems herein are configured to engage a thrombus in a patient's blood vessel, break the thrombus into small fragments, and aspirate the fragments out of the patient's body. The pressurized fluid streams (e.g., jets) function to cut or macerate thrombus, before, during, and/or after at least a portion of the thrombus has entered the aspiration lumen or a funnel of the system. Fragmentation helps to prevent clogging of the aspiration lumen and allows the thrombus removal system to macerate large, firm clots that otherwise could not be aspirated. As used herein, "thrombus" and "embolism" are used somewhat interchangeably in various respects. It should be appreciated that while the description may refer to removal of "thrombus," this should be understood to encompass removal of thrombus fragments and other emboli as provided herein.

According to embodiments of the present technology, a fluid delivery mechanism can provide a plurality of fluid streams (e.g., jets) to fluid apertures of the thrombus removal system for macerating, cutting, fragmenting, pulverizing and/or urging thrombus to be removed from a proximal portion of the thrombus removal system. The thrombus removal system can include an aspiration lumen extending at least partially from the proximal portion to the distal portion of the thrombus removal system that is adapted for fluid communication with an aspiration pump (e.g., vacuum source). In operation, the aspiration pump may generate a volume of lower pressure within the aspiration lumen near the proximal portion of the thrombus removal system, urging aspiration of thrombus from the distal portion.

FIG. 1 illustrates a distal portion 10 of a thrombus removal system according to an embodiment of the present technology. FIG. 1 includes cross-sectional lines A-A, B-B, and C-C, which are illustrated in FIG. 1A, FIG. 1B/1C, and FIG. 1D, respectively. FIG. 1A Section A-A illustrates an elevation sectional view of the distal portion. The example section A-A in FIG. 1A depicts a funnel 20 that is positioned at the distal end of the distal portion 10, the funnel adapted to engage with thrombus and/or a tissue (e.g., vessel) wall to aid in thrombus fragmentation and/or removal. The example section A-A in FIG. 1A depicts a double walled thrombus removal device construction having an outer wall/tube 40 and an inner wall/tube 50. An aspiration lumen 55 is formed by the inner wall 50 and is centrally located. A generally annular volume forms at least one fluid lumen 45 between the outer wall 40 and the inner wall 50. The fluid lumen 45 is adapted for fluid communication with a fluid delivery mechanism. One or more apertures (e.g., nozzles, orifices, or ports) 30 are positioned in the thrombus removal system to be in fluid communication with the fluid lumen 45 and an irrigation manifold 25. In operation, the ports 30 are adapted to direct (e.g., pressurized) fluid toward thrombus that is engaged with the distal portion 10 of the thrombus removal system. In some embodiments, the manifold can be positioned proximal to the funnel. In other embodiments, the manifold can be integrated into the funnel.

The thrombus removal system can be sized and configured to access and remove thrombi in various locations or vessels within a patient's body. It should be understood that while the dimensions of the system may vary depending on the target location, generally the same features and components described herein will be implemented in the thrombus removal system regardless of the application. For example, a thrombus removal system configured to remove pulmonary embolism (PE) from a patient may have an outer wall/tube with a size of approximately 11-13 Fr, or preferably 12 Fr, and an inner wall/tube with a size of 7-9 Fr, or preferably 8 Fr. A deep vein thrombosis (DVT) device, on the other hand, may have an outer wall/tube with a size of approximately 9-11 Fr, or preferably 10 Fr, and an inner wall/tube with a size of 6-9 Fr, or preferably 7.5 Fr. Applications are further provided for ischemic stroke and peripheral embolism applications.

Section B-B of FIG. 1B illustrates in plan view a portion of the thrombus removal system that is proximal to the funnel and irrigation manifold. Section B-B depicts an outer wall 140, an inner wall 150, an aspiration lumen 155 and a fluid lumen 145. As shown, the inner wall 150 forms the aspiration lumen, and the inner wall and outer wall are concentric to another. The fluid lumen 145 is formed in the space between the inner wall and outer wall. In some embodiments, in cross-section the aspiration lumen 155 is generally circular and the fluid lumen 145 is generally annular in shape (e.g., cross-section 70). It will be appreciated that alternative constructions and/or arrangements of the inner wall 150 and the outer wall 140 produce variations in cross-sectional shape of the aspiration and fluid lumens 155 and 145. For example, the inner wall 150 can be shaped to form an aspiration lumen 155 that, in cross-section, is generally oval, circular, rectilinear, square, pentagonal, or hexagonal. The inner and outer walls 150 and 140 can be shaped and arranged to form a fluid lumen 145 that, in cross-section, is generally crescent-shaped, diamond shaped, or irregularly shaped. For example, referring to FIG. 1C Section B-B, the region between the inner wall 150 and the outer wall 140 can include one or more wall structures 165 that form respective fluid lumens 145 (e.g., as in cross-section 80). The wall structures 165 can be formed by lamination between the outer and inner walls 140 and 150, or by a multi-lumen extrusion that forms a plurality of the wall structures.

Section C-C of FIG. 1D illustrates in plan view a portion of the thrombus removal system comprising an irrigation manifold 225. Section C-C depicts an outer wall 240, an inner wall 250, a fluid lumen 245, an aspiration lumen 255, and ports 230 for directing respective fluid streams 210.

Figures 1E, 2A, 2B, 2C, 2D, 2E:
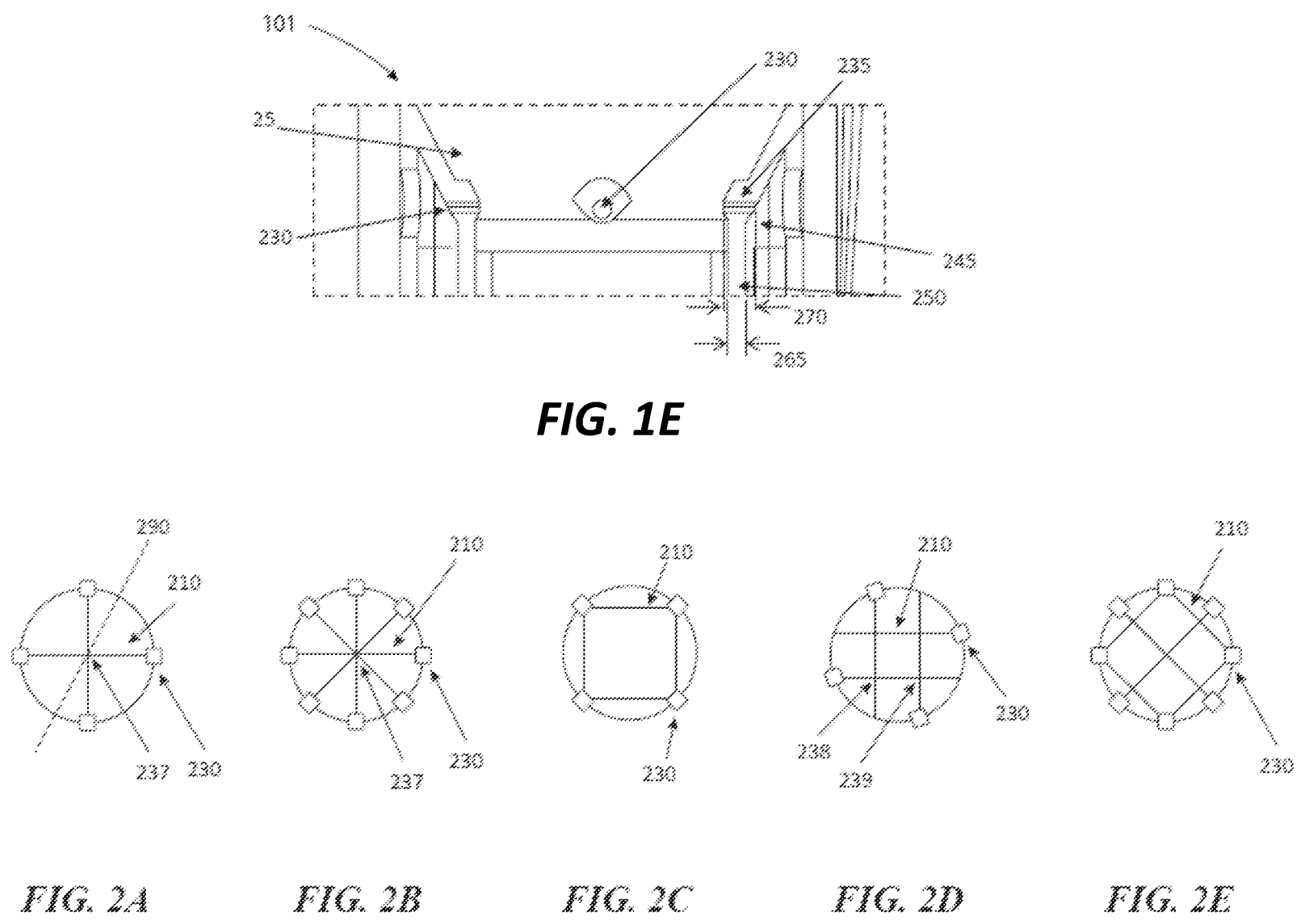

Detail View 101 of FIG. 1E illustrates a section view in elevation of a portion of the irrigation manifold 25 that includes a plurality of ports 230 that are formed within an inner wall 250. As shown, the manifold can be positioned at or near a distal end of the fluid lumen(s) formed by the inner and outer walls. In some embodiments, a thickness of one or more walls of the thrombus removal system may be varied along its axial length and/or its circumference. As shown in Detail View 101, inner wall 250 has a first thickness 265 in a region 250 that is proximal to the irrigation manifold 25, and a second thickness 270 in a region 235 that includes the ports 230. In some embodiments, the second thickness 270 is greater than the first thickness 265. The first thickness 265 can correspond to a general wall thickness of the inner wall 50 and/or of the outer wall 40, which can be from about 0.10 mm to about 0.60 mm, or any value within the aforementioned range. The second thickness 270 can be from about 0.20 mm to about 0.70 mm, from about 0.70 mm to about 0.90 mm, or from about 0.90 mm to about 1.20 mm. The second thickness 270 can be any value within the aforementioned range. The dimension of the second thickness 270 can be selected to provide a fluid path through the ports 230 that produces a generally laminar flow for a fluid stream that is directed therethrough, when the fluid delivery mechanism supplies fluid via the fluid lumen 245 at a typical operating pressure. Such operating pressure can be from about 10 psi to about 60 psi, from about 60 psi to about 100 psi, or from about 100 psi to about 150 psi. The operating pressure of the fluid delivery mechanism can be any value within the aforementioned range of values. In some embodiments, the fluid delivery mechanism is operated in a high pressure mode, having a pressure from about 150 psi to about 250 psi, from about 250 psi to about 350 psi, from about 350 psi to about 425 psi, or from about 425 psi to about 500 psi. The operating pressure of the fluid delivery mechanism in the high pressure mode can be any value within the aforementioned range of values.

The manifold is configured to increase a fluid pressure and/or flow rate of the fluid. When fluid is provided by the fluid delivery mechanism to the fluid lumen(s) at a first pressure and/or a first flow rate, the manifold is configured to increase the pressure of the fluid to a second pressure and/or is configured to increase the flow rate of the fluid to a second flow rate. The second pressure and/or second fluid rate can be higher than the first pressure and/or first flow rate. As a result, the manifold can be configured to increase the relatively low operating pressures and/or flow rates generated by the fluid delivery mechanism to the relatively high pressures and/or high flow rates generated by the ports/fluid streams.

In some embodiments, a profile (cross-sectional dimension) of a port 230 varies along its length (e.g., is non-cylindrical). A variation in the cross-sectional dimension of the port may alter and/or adjust a characteristic of fluid flow along the port 230. For example, a reduction in cross-sectional dimension may accelerate a flow of fluid through the port 230 (for a given volume of fluid). In some embodiments, a port 230 may be conical along its length (e.g., tapered), such that its smallest dimension is positioned at the distal end of the port 230, where distal is with respect to a direction of fluid flow.

In some embodiments, the port 230 is formed to direct the fluid flow along a selected path. FIGS. 2A-2E illustrate various embodiments of arrangements of ports 230 for directing respective fluid streams 210. In some embodiments, such as those shown in FIGS. 2A and 2B, at least two ports 230 are arranged to produce (e.g., respective) fluid streams 210 that intersect at an intersection region 237 of the thrombus removal system. An intersection region 237 can be a region of increased fluid momentum and/or energy transfer, which increase is with respect to individual fluid streams that are not directed to combine at the intersection. The increased fluid momentum and/or energy transfer at an intersection may advantageously fragment thrombus more efficiently and/or quickly. In some embodiments, an intersection region can be formed from at least 2, at least 3, at least 4, at least 5, at least 6, at least 7, at least 8, at least 9, or at least 10 fluid streams 210. An intersection region can be generally near a central axis 290 of the thrombus removal system (e.g., 237), or away from the central axis (e.g., 238 and 239 in the embodiment of FIG. 2D). In some embodiments, at least two intersection regions (e.g., 238 and 239) are formed. In some embodiments, one or more ports 230 are arranged to direct a fluid stream 210 along an oblique angle with respect to the central axis of the thrombus removal system. An operating pressure of the fluid delivery mechanism may be selected to approach a targeted fluid velocity for a fluid stream 210 that is delivered from a port 230. The targeted fluid velocity for a fluid stream 210 can be about 5 meters/second (m/s), about 8 m/s, about 10 m/s, about 12 m/s, about 10-15 m/s, or about 12-15 m/s. The targeted fluid velocity for fluid stream 210 can be any value within the range of aforementioned values. In some embodiments, at least two ports 230 are adapted to delivery respective fluid streams at different fluid velocities, for a given pressure of the fluid delivery mechanism. In some embodiments, at least two ports 230 are adapted to deliver respective fluid streams at the substantially the same fluid velocities, for a given pressure of the fluid delivery mechanism. In some embodiments, angular momentum is imparted to a thrombus by application of a) at least one fluid stream 210 that is directed at an oblique angle from a port 230, and/or b) at least two fluid streams 210 that have different fluid velocities. Advantageously, angular momentum produced in a thrombus may impart a (e.g., centrifugal) force that assists in fragmentation and removal of the thrombus. Advantageously, an increased cross-sectional area of the fluid lumen 145 reduces a required operating pressure of the fluid delivery mechanism to achieve a targeted fluid velocity of the fluid streams.

Referring to FIGS. 3A-3H, ports 330 can be arranged along various axial positions of the thrombus removal system. The thrombus removal system can include a flow axis 305 that is aligned with a general direction (e.g., distal-to-proximal) of flow for fluid that is aspirated therein. In some embodiments, a position of a port 330 comprises a) near a base of, b) in a middle portion of, c) in a distal portion of, or d) proximal to, a funnel portion 320 of the thrombus removal system. Although the embodiments illustrated herein show only a single port 330, it should be understood that any of these embodiments can include multiple ports arranged around the funnel or proximal to the funnel. For example, any of the port arrangements illustrated in FIGS. 2A-2E can be implemented a) near a base of, b) in a middle portion of, c) in a distal portion of, or d) proximal to, a funnel portion 320 of the thrombus removal system.

Figure 3D:
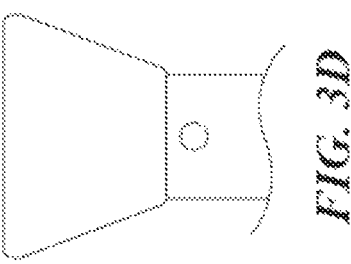
FIGS. 3A-3H illustrate an elevation view of various configurations of irrigation ports of a thrombus removal system according to embodiments of the present technology.
Figure 3H:
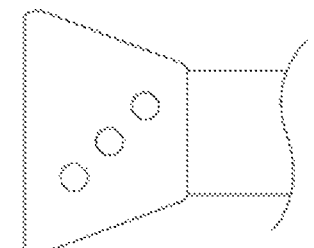
Figure 3C:
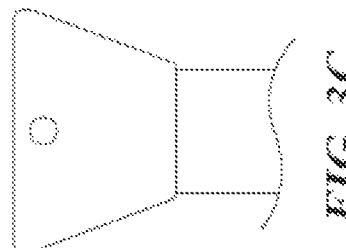
Figure 3G:
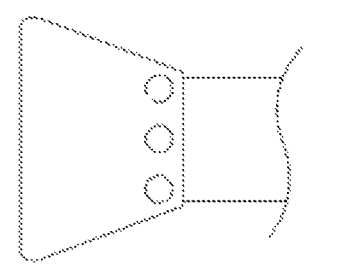
Figure 3B:
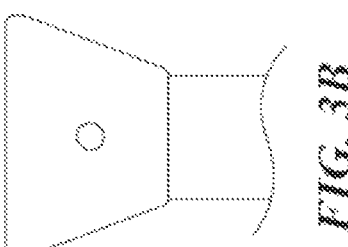
Figure 3F:
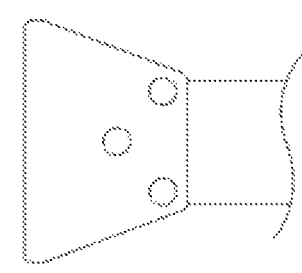
Figure 3A:
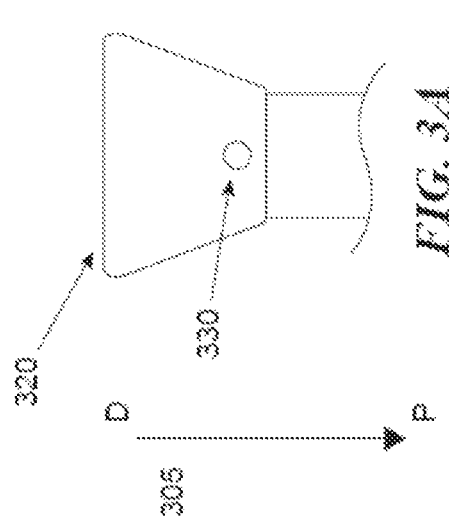
Figure 3E:
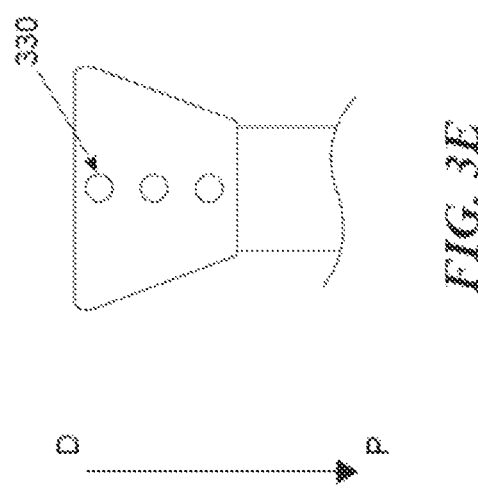

In some embodiments, at least two ports 330 are aligned along flow axis 305 (e.g., FIG. 3E). In some embodiments, at least two ports 330 are arranged at a different axial position along the flow axis 305 (e.g., FIGS. 3F, 3G, 3H). In some embodiments, at least two ports 330 are arranged (e.g., along a perimeter of the thrombus removal system) along a given axial position of the flow axis 305. As with above, any of the port arrangements illustrated in FIGS. 2A-2E can be implemented into the port arrangements illustrated in the embodiments of FIGS. 3F, 3G, and 3H.

FIGS. 4A-4H depict various configurations of fluid streams 410 that are directed from respective ports 430. A fluid stream 410 can be directed along a path that is substantially orthogonal (e.g., FIG. 4A), proximal (e.g., FIG. 4C), and/or distal (e.g., FIG. 4B) to the flow axis 405 (which is like to flow axis 305). In some embodiments, at least two fluid streams are directed in different directions with respect to the flow axis 405 (e.g., FIG. 4E). In some embodiments, at least one fluid stream is directed in a same direction (e.g., distally) with respect to the flow axis 405 and at least another fluid stream is directed in a different direction (e.g., orthogonally or proximally, as shown in FIG. 4D). In some embodiments, at least a first fluid stream is directed substantially orthogonally to the flow axis, at least a second fluid stream is directed proximally, and at least a third fluid stream is directed distally with respect to the flow axis 405. An angle α may characterize an angle α fluid stream 410 is directed with respect to an axis that is orthogonal to the flow axis 405 (e.g., as shown in section D-D of FIGS. 4G and 4H). An intersection region of fluid streams can be within an interior portion of the thrombus removal system, and/or exterior (e.g., distal) to the thrombus removal system. In some embodiments, a fluid stream that is directed by a port 430 in a nominal direction (e.g., distally) is deflected along an altered path (e.g., proximally) by (e.g., suction) pressure generated by the aspiration mechanism during operation.

FIGS. 5A-5G illustrate a variety of exit aperture geometries with which ports 530 can be configured in accordance with embodiments of the present technology. Aperture geometries can comprise an oval, circular, cross ("x" shape), "t" shape, rectangle, or square shape. A fluid stream that is delivered from the port 530 can comprise substantially laminar flow (e.g., at the aperture), or a turbulent flow (e.g., that fans or outward). For example, FIG. 5B shows a "x" shaped exit aperture geometry. FIG. 5C shows a "t" shaped exit aperture geometry. FIGS. 5D-5G show variations of an oval shaped exit aperture geometry. As shown in FIG. 5D, the fluid stream can be substantially laminar flow, and in FIG. 5E, the flow can fan outward.

Figure 6:
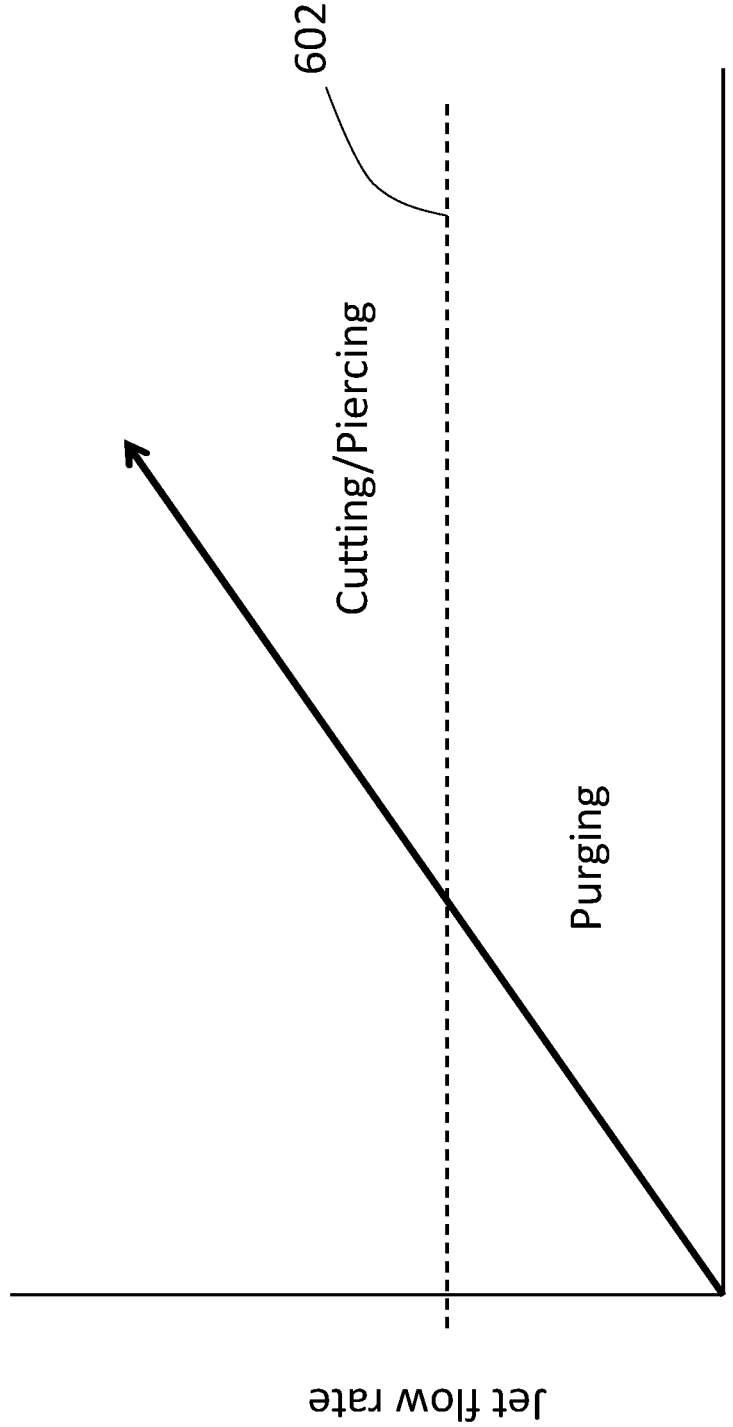
FIG. 6 is a diagram showing a relationship between jet flow rate and interaction with one or more clots.

Referring to FIG. 6, a chart is provided that illustrates the relationship between the exit velocity or flow rate (avg.) of the jet(s) and the mechanism of action with one or more thrombi engaged with the thrombus removal device (i.e., engaged in the funnel or with the aspiration lumen). Generally, at lower jet flow rates (e.g., below 10 m/s depending on different parameters like the formulation of the clot and the jet configuration), the jets serve to assist with purging of the thrombus or thrombi into the aspiration lumen (especially when the funnel is occluded or partially occluded by the clot). This purging can include the function of pushing the thrombus into and or through the aspiration lumen and also providing fluid into the funnel and into the aspiration lumen to assist with clot removal. The purging may also assist with breaking up soft, loose material on the surface of the clot but it will not be able to break through harder material. However, once the jet flow rate begins to exceed a cutting threshold 602, the jets begin to cut the thrombus or thrombi surface to break the thrombus into small fragments which can then be more easily aspirated into the aspiration lumen of the thrombus removal device. It has also been found that at sufficiently high velocity the jet(s) will pierce the clot surface and penetrate through to the inner part of the clot. In some embodiments, the threshold comprises a jet flow rate that ranges from 10-12 m/s. In other embodiments, an ideal cutting or piercing flow rate of the jets range from 10-15 m/s, or alternatively, from 12-15 m/s.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A thrombus removal system, comprising:
an elongated catheter device including:
a distal portion configured to be positioned within a blood vessel of a patient, the distal portion comprising an inner wall forming an aspiration lumen, and an outer wall, and a fluid lumen formed in a space between the inner wall and the outer wall;
a manifold formed near a distal end of the fluid lumen and the aspiration lumen, the manifold including a first fluid port and a second fluid port formed therein and surrounded by the manifold, the first fluid port having a first axis, the second fluid port having a second axis, wherein the first axis intersects with the second axis at a fluid intersection within the distal portion, the first fluid port and the second fluid port being configured to direct respective fluid streams along the first axis and the second axis that collide at the fluid intersection within the distal portion;
a proximal portion configured to be positioned external to the patient, the aspiration lumen extending from the distal portion to the proximal portion;
an aspiration mechanism positioned external to the patient and fluidly coupled with the aspiration lumen, the aspiration mechanism configured to reduce a pressure at the distal portion (a) to engage a thrombus therewith and/or (b) to draw the thrombus and/or thrombus fragments proximally; and
a fluid delivery mechanism configured to supply fluid through the fluid lumen.

2. The system of claim 1 wherein the inner wall and the outer wall are concentrically arranged such that the fluid lumen is generally annular in cross-section.

3. The system of claim 1, further comprising at least one fluid wall disposed in the space between the inner and outer walls, the at least one fluid wall forming the fluid lumen.

4. The system of claim 1, wherein the manifold is formed from the inner wall and the outer wall.

5. The system of claim 1, wherein the first fluid port and the second fluid port are formed within the inner wall of the manifold.

6. The system of claim 5, wherein the inner wall has a first thickness in a first region within the manifold, and a second thickness proximal to the first region.

7. The system of claim 6, wherein the first thickness is greater than the second thickness.

8. The system of claim 7, wherein the first thickness is about twice that of the second thickness.

9. The system of claim 6, wherein the first thickness ranges from 0.10 mm to 0.60 mm and the second thickness ranges from 0.20 mm to 0.70 mm.

10. The system of claim 6, wherein the first thickness is selected to provide a generally laminar flow for the respective fluid streams.

11. The system of claim 1, wherein a cross-sectional dimension of the first fluid port and the second fluid port varies along its length.

12. The system of claim 11, wherein the first fluid port and the second fluid port are conical along their lengths.

13. The system of claim 12, wherein a smallest dimension of the first fluid port and the second fluid port is positioned at a distal end of the two or more ports.

14. The system of claim 1, wherein the manifold is configured to increase a flow rate of the fluid in the fluid lumen.

15. The system of claim 1, wherein the manifold is configured to increase a pressure of the fluid in the fluid lumen.

16. The system of claim 1, further comprising a funnel positioned at a distal end of the distal portion, the funnel being configured to engage with the thrombus.

17. The system of claim 16, wherein the manifold is disposed proximally of the funnel.

18. The system of claim 16, wherein the manifold is integrated into the funnel.

* * * * *